(12) United States Patent
Bunce

(10) Patent No.: US 6,371,918 B1
(45) Date of Patent: Apr. 16, 2002

(54) TRANSDUCER CONNECTOR

(75) Inventor: Steven Bunce, Sedro Wooly, WA (US)

(73) Assignee: SonoSite Inc., Bothell, WA (US)

( * ) Notice: Subject to any disclaimer, the term of this patent is extended or adjusted under 35 U.S.C. 154(b) by 0 days.

(21) Appl. No.: 09/564,602

(22) Filed: May 3, 2000

Related U.S. Application Data

(60) Provisional application No. 60/132,664, filed on May 5, 1999.

(51) Int. Cl.[7] .................................................. A61B 8/14
(52) U.S. Cl. ........................................ 600/459; 439/261
(58) Field of Search ................................ 600/437, 438, 600/440–447, 459; 439/259, 261, 262, 264, 372, 310, 953

(56) References Cited

U.S. PATENT DOCUMENTS

| | | | |
|---|---|---|---|
| 3,648,002 A | 3/1972 | DuRocher | 200/166 C |
| 3,950,058 A | 4/1976 | Cronin | 339/75 M |
| 5,368,496 A | 11/1994 | Ranalletta et al. | 439/261 |
| 5,554,045 A | 9/1996 | Bethurum | 439/372 |
| 5,882,310 A | * 3/1999 | Marian, Jr. | 600/459 |
| 5,997,479 A | * 12/1999 | Savord et al. | 600/447 |

* cited by examiner

*Primary Examiner*—Marvin M. Lateef
*Assistant Examiner*—Ali M. Imam
(74) *Attorney, Agent, or Firm*—Townsend and Townsend and Crew LLP; Henry K. Woodward

(57) ABSTRACT

Disclosed is a transducer connector which overcomes limitations in the prior art by allowing significant reduction in connector size and weight. Key attributes of this invention are electrical contacts incorporated onto a printed circuit board, a folding latch assembly, and the use of lightweight, rigid materials for fabrication. Additionally, the mating half of the connector may be mounted directly on a printed circuit board implementing circuitry for a diagnostic ultrasound instrument, thus saving weight, volume, and complexity.

15 Claims, 7 Drawing Sheets

TRANSDUCER CONNECTOR

The application claims the benefit of provisional application 60/132,664 filed May 5, 1999.

BACKGROUND OF THE INVENTION

This invention relates generally to medical ultrasonic diagnostic systems, and more particularly this invention relates to ultrasonic diagnostic instruments which employ detachable ultrasound transducer scanheads.

Modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., were smaller desktop units about the size of a personal computer. However, such instruments lack many of the advanced features of today's premium ultrasound systems such as color Doppler imaging and three dimensional display capabilities. As ultrasound systems become more sophisticated they also become bulkier.

Disclosed in U.S. Pat. No. 5,722,412 is a diagnostic ultrasound instrument which exhibits many of the features of a premium ultrasound system in an hand-held unit. The instrument can be produced as a single unit or in a preferred embodiment the instrument is a two-part unit one including a transducer, beamformer, and image processor and the other including a display and power source for both units. In such a configuration the transducer/processor unit can be manipulated with one hand while a cable between the two units enables the video to be shown on the display unit while the lateral unit is held or positioned for optimal viewing of the ultrasound image. The cable also provides energy for the transducer/processor unit from the display unit.

The transducer connector is a critical component in a diagnostic ultrasound device. In previous implementations, large, heavy connectors were designed which were quite reliable and maintained good signal fidelity. The disadvantages of size and weight were not of primary significance for larger scanning devices. In the case of a small, highly portable ultrasound scanner, however, size and weight are of primary importance, and existing technology was not adequate. Ideally, the connector for a highly portable scanner should be light weight and have a very low physical profile to conserve space. The present invention has these attributes.

SUMMARY OF THE INVENTION

The present invention overcomes limitations in the prior art by providing a transducer connector design that allows a significant reduction in connector size and weight. Key attributes of this invention are electrical contacts incorporated onto a printed circuit board, a folding latch assembly, and the use of lightweight, rigid materials for fabrication. Additionally, the mating half of the connector may be mounted directly on a printed circuit board implementing circuitry for a diagnostic ultrasound instrument, thus saving weight, volume, and complexity.

The printed circuit board of the mating half can include necessary electronics including one or more of a beamformer, signal processing circuitry, and a Doppler processor.

The invention and objects and features thereof will be more readily apparent from the following detailed description and appended claims when taken with the drawings.

DESCRIPTION OF THE SPECIFIC EMBODIMENTS

Figure 1:
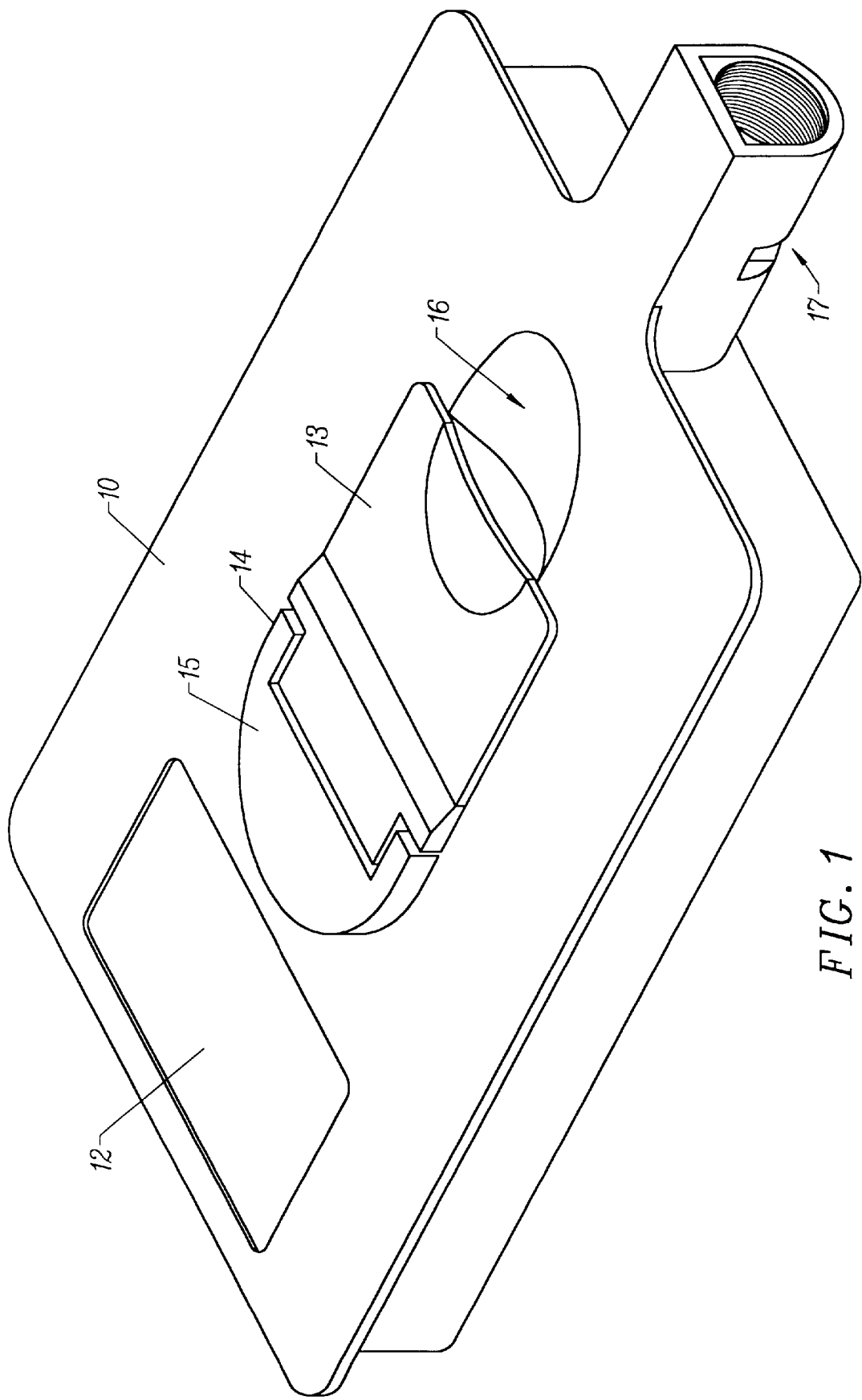
FIG. 1 is a perspective view of the back of an embodiment of the connector in accordance with the invention.

In FIG. 1 the connector housing is shown assembled. Housing 10 incorporating label depression 12 supports the latch assembly. The latch is shown in the closed and locked position. Handle 13 is folded down against housing 10, and is attached to a rotating retainer 15 via hinge 14. Depression 16 allows the handle to be easily folded up by providing a space for a finger to pull on the handle 13. Conduit 17 receives the cable to the transducer.

Figure 1A:
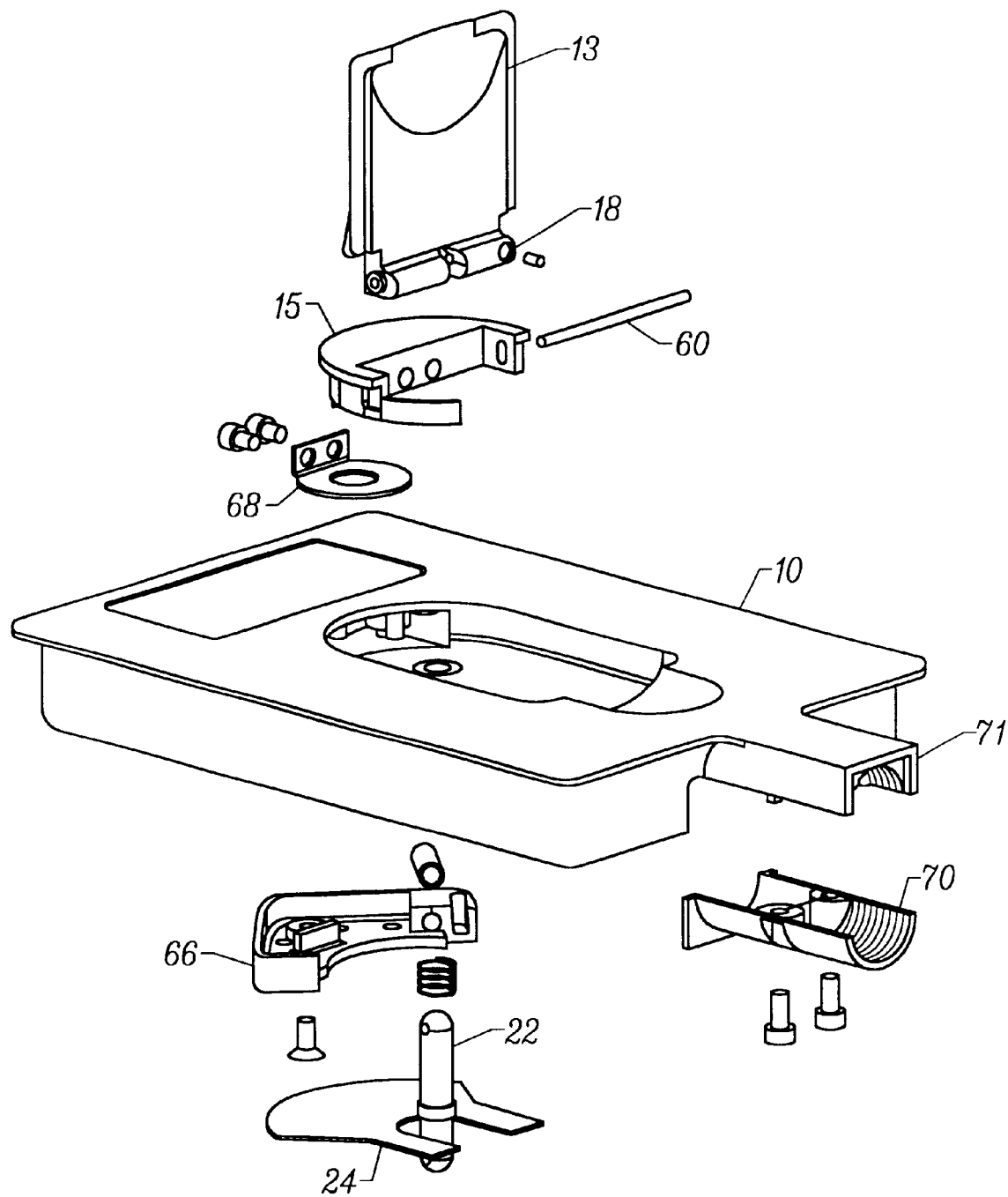
FIG. 1A is an exploded perspective view of the latch mechanism in the connector of FIG. 1.

FIG. 1A is an exploded perspective view of the latch assembly in the connector of FIG. 1. Handle 13 is attached by a pin 22 to base retainer 15 with pin 60 received in cam 18. A mating base member 66 receives pin 22 and spring clip 24 which biases the rotation of handle 13. Guide 68 is fastened to retainer 15 for aligning pin 22 which is received in cam 18. Bottom conduit 70 mates with upper conduit 71 to form cable conduit 17 of FIG. 1.

Figure 2:
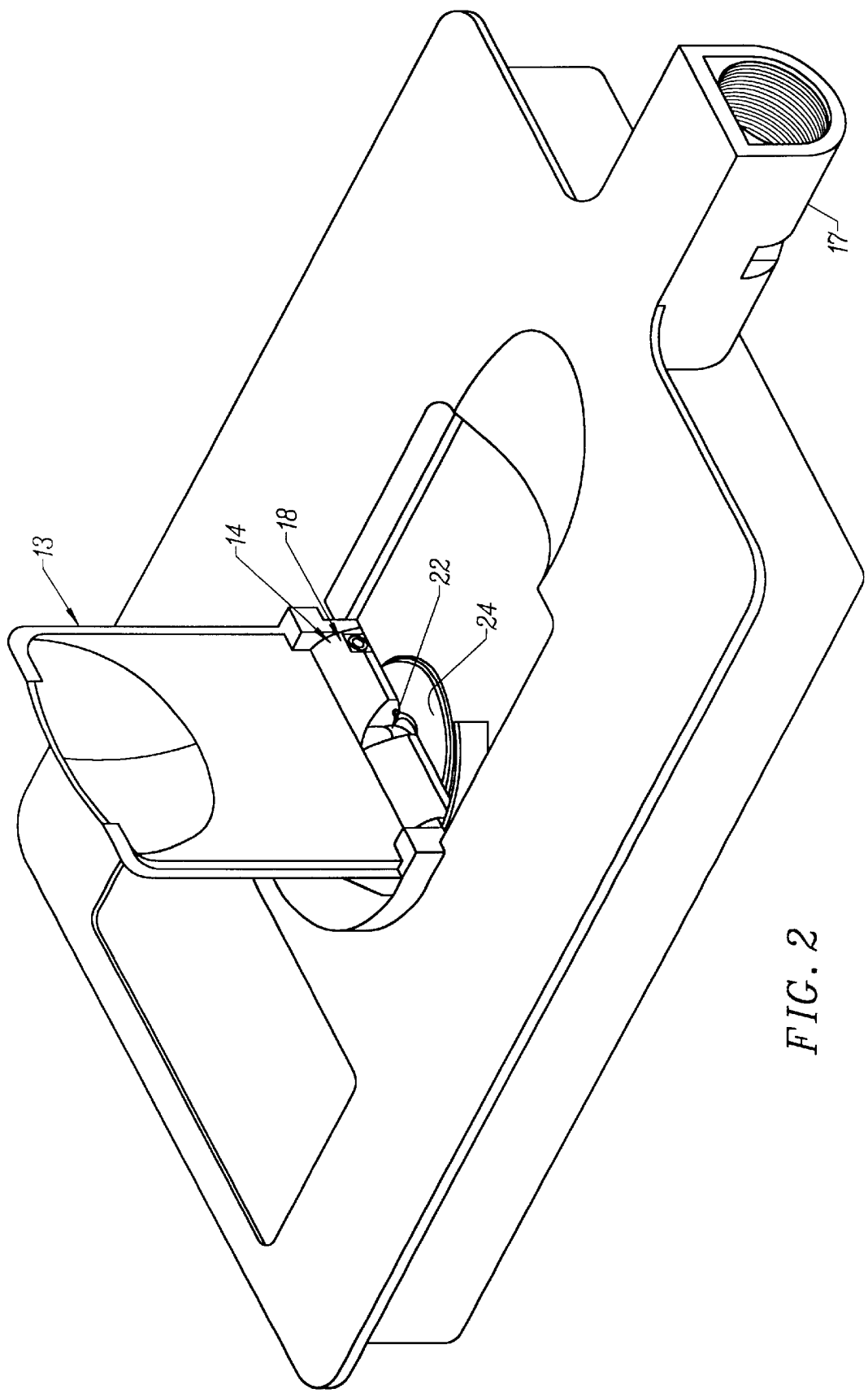
FIG. 2 is the same view as in FIG. 1, but with the latch handle raised.

In FIG. 2, the handle 13 is now shown in the open position, folded up on hinge 14. Cam 18 is attached to handle 13 and allows center pin 22 to drop, releasing pressure holding this side of the connector to the mating side. Spring clip 24 provides a positive action.

Figure 3:
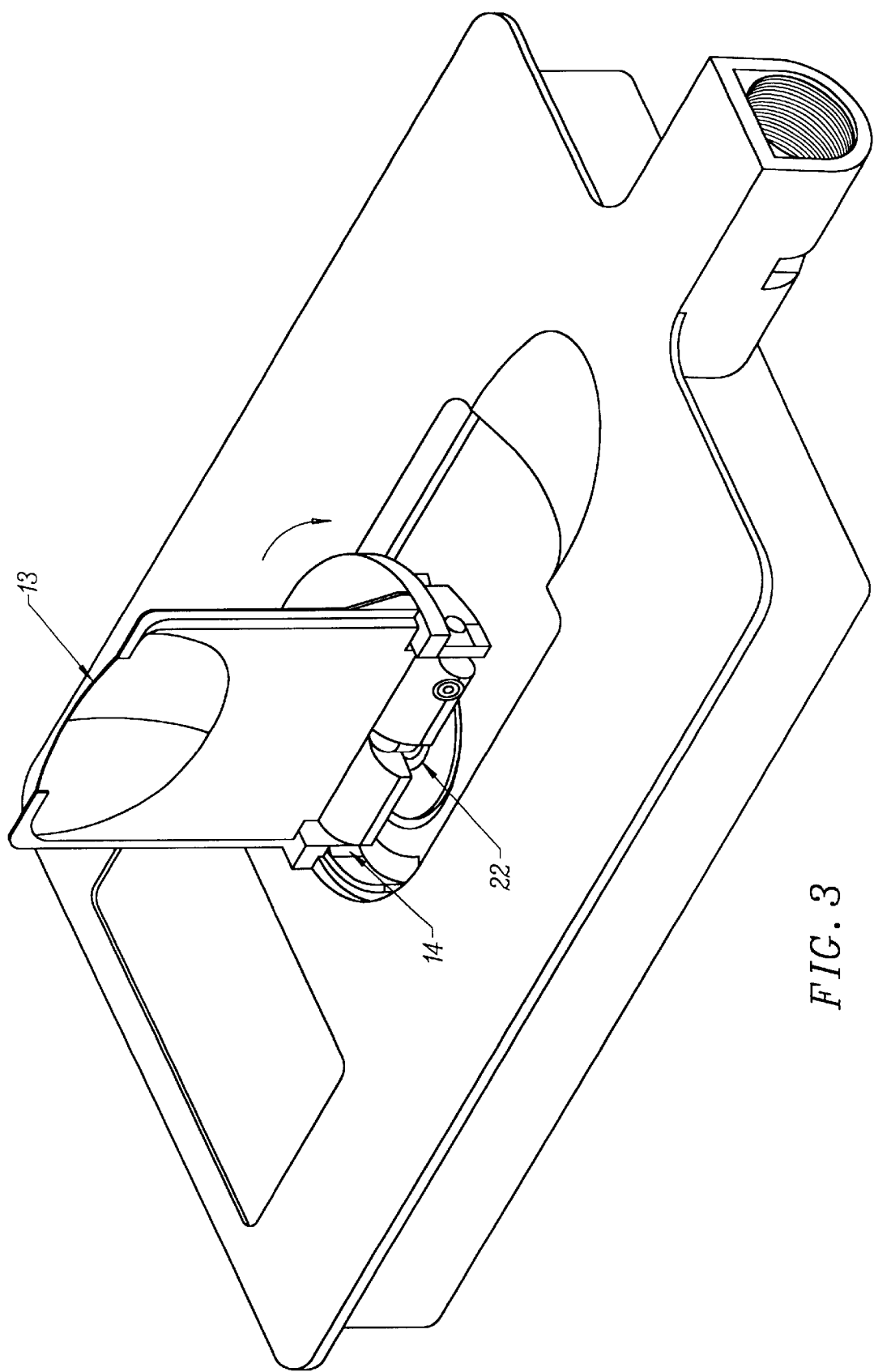
FIG. 3 is the same view as in FIG. 2, but with the latch handle rotated for release of the connector.

In FIG. 3, the handle 13 is shown rotated along with center pin 22, which allows the connector to be disengaged from the mating side.

Figure 4:
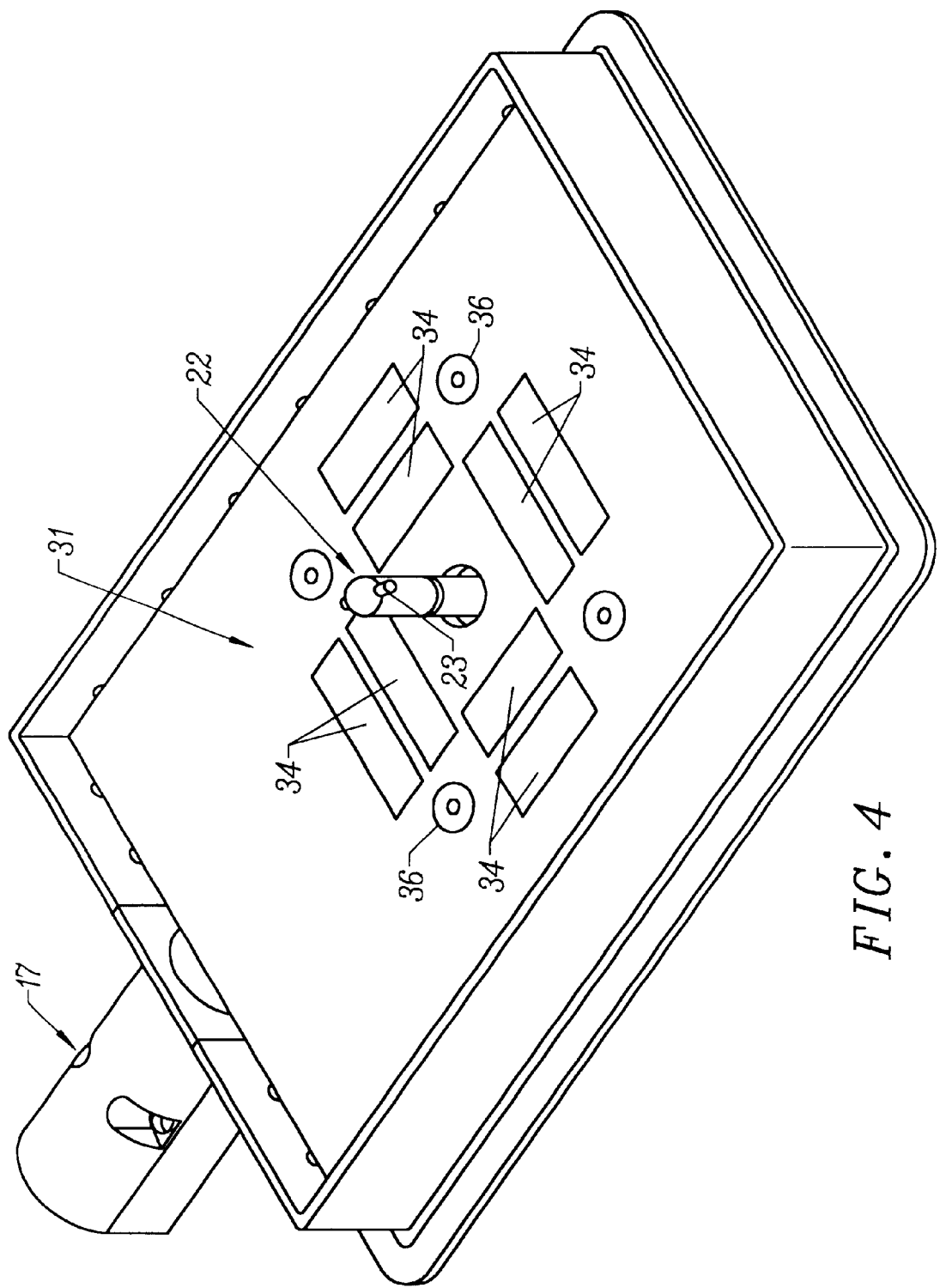
FIG. 4 is a perspective view of the front of an embodiment of the connector of FIG. 1 illustrating significant features.
Figure 5:
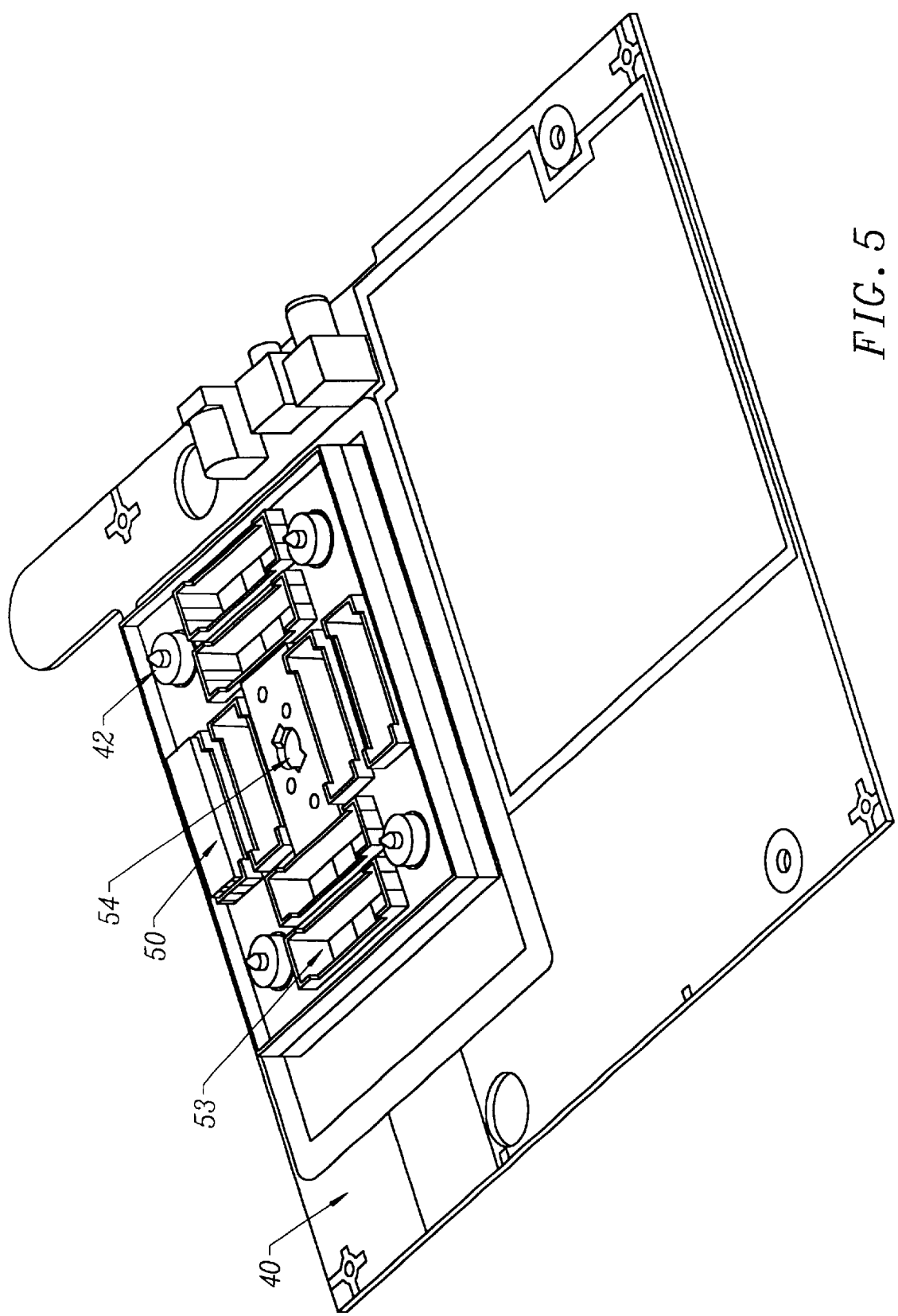
FIG. 5 shows the mating portion of the connector mounted on a printed circuit board implementing circuitry of a diagnostic ultrasound instrument.

FIG. 4 shows the bottom of the connector housing 10, showing center pin 22 incorporating retaining pins 23 protruding through connector board 31. The connector board is a printed-circuit board with gold plated contacts shown generally at groups 34 that connect with interposer connectors on a mating connector of the console as shown in FIG. 5. Electrical connection between the transducer and the connector board is made via a cable that enters through conduit 17. Guides 36 receive alignment pins of the mating connection.

FIG. 5 shows the mating connector mounted on printed circuit board 40 of the module. Alignment pins 42 help to guide the two halves 31, 40 into proper position by mating with guides 36. Interposer connector assemblies 50 fit into pin slots 53 and provide electrical contact with contacts 34 on the printed circuit board 31 in FIG. 4. Center pin 22 in FIG. 4 fits through hole 54 which allows passage of retaining pins 33 if rotated correctly.

Figure 6:
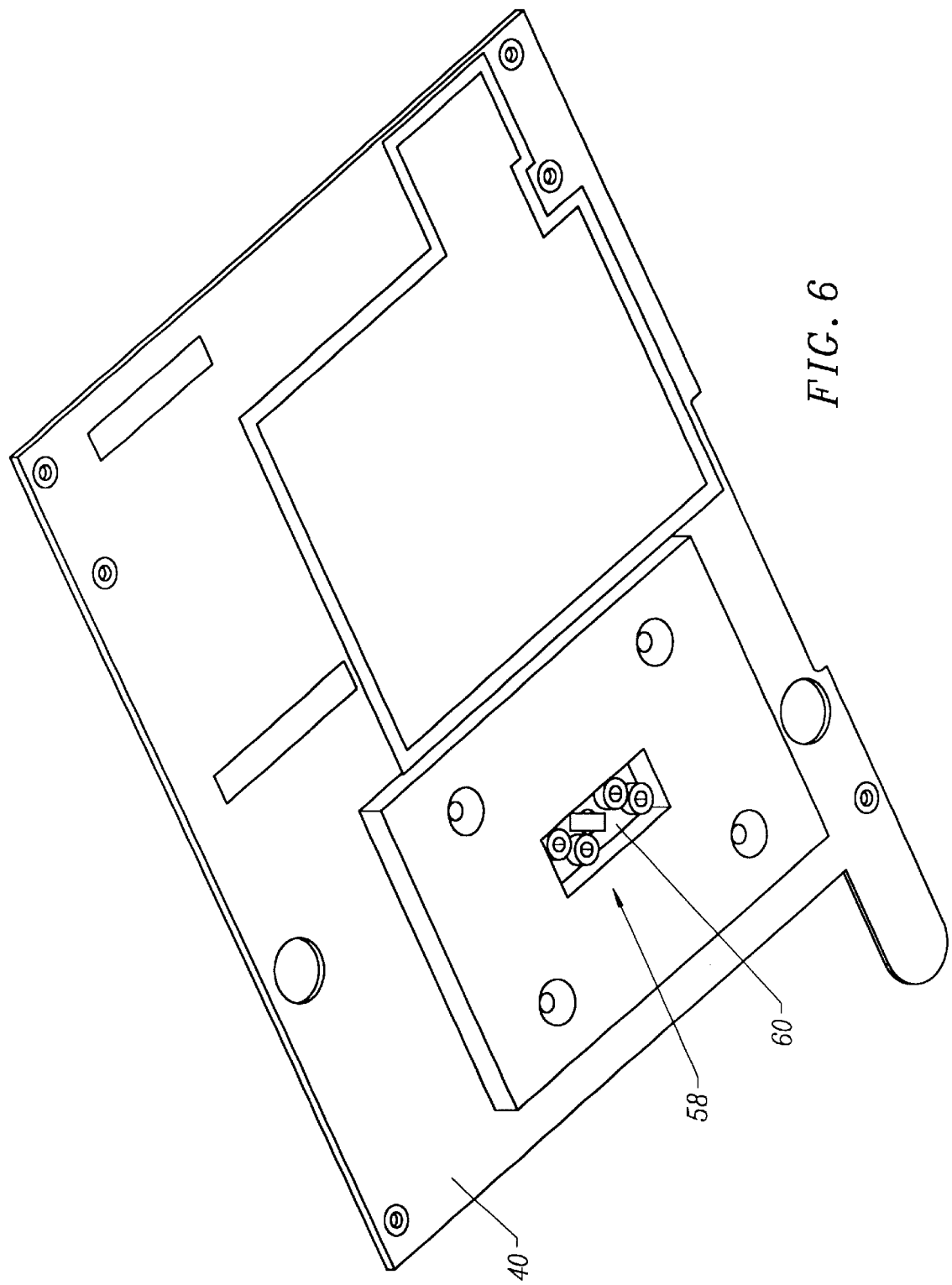
FIG. 6 is a perspective view illustrating the back side of the connector of FIG. 5.

FIG. 6 shows the back of the printed circuit board 40 illustrating backing plate 58 which is required to maintain the rigidity of the connector assembly, and thrust plate 60 which retaining pins 33 pull against to ensure proper seating of the connector.

In the preferred embodiment, the bulk of the connector components are made from magnesium, which is a strong, light weight material. The overall height of the connector can be less than three quarters of inch, and 63, 127 or greater number of contacts can be accommodated.

There has been described a transducer connector intended for use with a diagnostic ultrasound system which overcomes limitations of the prior art through its design. While the invention has been described with reference to a specific embodiment, the description is illustrative of the invention and is not to be construed as limiting the invention. For example, electrical connection may be made through conductive devices other than an interposer assembly, and the connector itself may be made of materials other than metal. Thus, various modifications and applications may occur to those skilled in the art without departing from the true spirit and scope of the invention as defined by the appended claims.

What is claimed is:

1. A transducer connector comprising
   a) a housing having a first assembly having contacts which interconnect with a second assembly, and
   b) a latch mechanism for securing the first and second assemblies including a handle mounted on the first assembly which folds flush with the first assembly when locked and which pivots to a raised position and rotates for unlocking the assemblies, the handle being coupled to a pin which engages the second assembly in a locked position, the handle being rotated in the raised position for disengaging the pin from the second assembly.

2. The transducer connector of claim 1 where the overall height of the connector is less than one inch.

3. The transducer connector of claim 1 where the overall height of the connector is less than three quarters of one inch.

4. The transducer connector of claim 1 where electrical contacts are incorporated directly onto a printed circuit board in the first assembly.

5. The transducer connector of claim 1 where a transducer cable exits the connector from a side of the connector housing.

6. The transducer connector of claim 5 where the number of electrical contacts is greater than 63.

7. The transducer connector of claim 5 where the number of electrical contacts is greater than 127.

8. The transducer connector of claim 1 where the connector is used with a transducer containing no active electronics.

9. The transducer connector of claim 1 where the connector is used with a transducer containing active electronics.

10. The transducer connector of claim 1 where the mating portion of the second assembly is mounted on a printed circuit board.

11. The transducer connector of claim 10 where said printed circuit board includes beamforming circuitry.

12. The transducer connector of claim 10 where said printed circuit board includes signal processing circuitry.

13. The transducer connector of claim 10 where said printed circuit board includes a Doppler processor.

14. The transducer connector of claim 1 where a depression is incorporated in the connector housing to facilitate unlatching the handle by allowing improved access for the operator's finger.

15. The transducer connector of claim 1 wherein the housing is made from magnesium.

* * * * *